(12) United States Patent
Jeong et al.

(10) Patent No.: US 12,263,199 B2
(45) Date of Patent: Apr. 1, 2025

(54) **USE OF *SIDA RHOMBIFOLIA***

(71) Applicants: INDUSTRY-ACADEMIC COOPERATION FOUNDATION GYEONGSANG NATIONAL UNIVERSITY, Jinju-Si (KR); KOREA RESEARCH INSTITUTE OF BIOSCIENCE AND BIOTECHNOLOGY, Daejeon (KR)

(72) Inventors: Eun Ju Jeong, Jinju-si (KR); Sangho Choi, Daejeon (KR); Randall Garcia Viquez, Santo Domingo (CR); Silvia Soto Montero, Santo Domingo (CR); Soo-Yong Kim, Daejeon (KR); Dong-Keun Yi, Daejeon (KR); Nelson Zamora Villalobos, Santo Domingo (CR)

(73) Assignees: INDUSTRY-ACADEMIC COOPERATION FOUNDATION GYEONGSANG NATIONAL UNIVERSITY, Jinju-Si (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 788 days.

(21) Appl. No.: 17/423,078

(22) PCT Filed: Jan. 15, 2020

(86) PCT No.: PCT/KR2020/000751
§ 371 (c)(1),
(2) Date: Jul. 14, 2021

(87) PCT Pub. No.: WO2020/149645
PCT Pub. Date: Jul. 23, 2020

(65) Prior Publication Data
US 2022/0080010 A1    Mar. 17, 2022

(30) Foreign Application Priority Data

Jan. 16, 2019 (KR) .................. 10-2019-0005875
Jan. 14, 2020 (KR) .................. 10-2020-0004754

(51) Int. Cl.
*A61K 36/185* (2006.01)
*A23L 33/105* (2016.01)
*A61P 13/08* (2006.01)

(52) U.S. Cl.
CPC .......... *A61K 36/185* (2013.01); *A23L 33/105* (2016.08); *A61P 13/08* (2018.01)

(58) Field of Classification Search
None
See application file for complete search history.

(56) References Cited

U.S. PATENT DOCUMENTS

2007/0178202 A1    8/2007   Verbruggen et al.

FOREIGN PATENT DOCUMENTS

| CN | 106309595 A | * | 1/2017 |
| WO | 2015111832 A1 | | 7/2015 |

OTHER PUBLICATIONS

Watson ("What's the Difference Between BPH and Prostate Cancer?"—internet archived version from Aug. 2017—https://web.archive.org/web/20170822235312/http://www.healthline.com/health/mens-health/bph-vs-prostate-cancer#causes3 ).*
Wang et.al., "Establishment of a Novel Model for Studying the Effects of Extracts of Chinese Herb Medicine on Human Type II 5α-Reductase in Vitro", Yakugaku Zasshi, 2010, pp. 1207-1214, 130(9).
Gupta SR et al., "Anti-arthritic activity of various extracts of Sida rhombifolia aerial parts", Natural Product Research: Formerly Natural Product Letters, 2009, pp. 689-695, vol. 23 No. 8.
Shinde et.al., "Hypoglycemic and Hypolipidemic Effect of *Sida rhombifolia* ssp. *retusa* in Diabetic Induced Animals", International Journal of Phytomedicine 2, 2010, pp. 160-165.
Os et al., "Alkaloids and Phenolic Compounds from *Sida rhombifolia* L. (Malvaceae) and Vasorelaxant Activity of Two Indoquinoline Alkaloids", Molecules, 2017, pp. 1-9, vol. 22.
Mah et al., "Anti-inflammatory, anti-cholinergic and cytotoxic effects of Sida rhombifolia", Pharmaceutical Biology, 2017, pp. 920-928, vol. 55, No. 1.
Bati et al., "The inhibitory effect of an ethanol extract of sida rhombifolia leaves on key carbohydrate hydrolyzing enzymes", Journal of Complementary Medicine Research, 2018, pp. 1-10, vol. 9, No. 1.
Singh et al., "Traditional uses, antimicrobial potential, pharmacological properties and phytochemistry of Sida rhombifolia linn. : A review", International Journal of Innovative Pharmaceutical Sciences and Research, 2018, pp. 54-68, vol. 6, No. 2.
Nahata et al., "Evaluation of 5α-reductase inhibitory activity of certain herbs useful as antiandrogens", Andrologia, 2014, pp. 592-601, vol. 46.
Jeong et al., "The effects of *Sida rhombifoia* L. on benign prostatic hyperplasia in testosterone propionate-induced animal model and its active constituents", Planta Med, 2019, <URL: https://www.thieme-connect.com/products/ejournals/html/10.1055/s-0039-3400097>.
Jasmeet Kaur Abat et al., "Ethnomedicinal, Phytochemical and Ethnopharmacological Aspects of Four Medicinal Plants of Malvaceae Used in Indian Traditional Medicines: A Review", Oct. 18, 2017, pp. 1-33, vol. 4.
Rao et al., "Anti-Inflammatory and Hepatoprotective Activities of Sida Rhombifolia Linn.", Indian Journal of Pharmacology, 1997, pp. 110-116, vol. 29.

* cited by examiner

*Primary Examiner* — Susan Hoffman
(74) *Attorney, Agent, or Firm* — NKL LAW; Jae Youn Kim

(57) ABSTRACT

Proposed is a novel use of *Sida rhombifolia*, which provides the benefit of effectively treating, ameliorating, inhibiting, and/or preventing benign prostatic hyperplasia.

4 Claims, 3 Drawing Sheets

USE OF *SIDA RHOMBIFOLIA*

TECHNICAL FIELD

The present disclosure relates to *Sida rhombifolia* and, more particularly, to a novel use of *Sida rhombifolia*.

BACKGROUND ART

Benign prostatic hyperplasia (BPH) is one of the most common male urinary diseases and refers to a condition in which the prostate around the urethra becomes abnormally enlarged to block the discharge of urine, thereby causing various symptoms. It is known that one of the causes of benign prostatic hyperplasia caused by prostatic cell proliferation is associated with the secretion of male hormones, judging from the fact that the symptoms of benign prostatic hyperplasia mainly appear after the age of 50, and the disease occurs only when male hormone is secreted normally since puberty.

The main male hormone involved in the growth of prostate tissue is dihydrotestosterone (DHT). DHT is the converted form of testosterone by 5-alpha reductase (5AR). 5AR is a 3-oxo-5α-steroid 4-dehydrogenase that is a nicotinamide adenine dinucleotide phosphate (NADPH) (reduced form)-dependent protein in the microsome and reduces steroids such as testosterone that contains double bonds.

There are two types of 5AR in the body: 5ARI (Type I, Type 1) and 5AR2 (Type II, Type 2). SARI is mainly expressed in the liver, adrenal glands, and skin, and 5AR2 is mainly expressed in the prostate. 5AR2 is known to play an important role in the pathogenesis of BPH. It is known that when 5AR2 is overexpressed and the concentration of DHT increases, a large amount of DHT binds to androgen receptor (AR) and causes prostatic hypertrophy. Therefore, it is known that finding an inhibitor of 5AR (in particular, 5AR2) is important in the treatment of prostatic hypertrophy {see, Xingsheng Wang et. al., "Establishment of a Novel Model for Studying the Effects of Extracts of Chinese Herb Medicine on Human Type II 5α-Reductase in Vitro", YAKUGAKU ZASSHI 130(9) 1207-1214, (2010) et al.}.

On the other hand, *Sida rhombifolia* belongs to the order Malvales, the family Malvaceae, and inhabits in Korea, Japan, subtropical regions, and tropical regions. It has been reported that such *Sida rhombifolia* is effective in ameliorating arthritis (see, Gupta S R et al., "Anti-arthritic activity of various extracts of *Sida rhombifolia* aerial parts", Natural Product Research: Formerly Natural Product Letters, 23:8, 689-695 (2009)) and treating diabetes (see, Vaibhav M. Shinde et. al., "Hypoglycemic and Hypolipidemic Effect of *Sida rhombifolia* ssp. *retusa* in Diabetic Induced Animals", International Journal of Phytomedicine 2 (2010) 160-165), and recently, it has been known that *Sida rhombifolia* has a vasodilatory effect {see, Chaves O S et al., "Alkaloids and Phenolic Compounds from *Sida rhombifolia* L. (Malvaceae) and Vasorelaxant Activity of Two Indoquinoline Alkaloids". Molecules 2017; 22:1-9, etc.}, so related technological development is required.

PRIOR ART LITERATURES

Non-Patent Literatures (non-patent literature 0001) Xingsheng Wang et. al., "Establishment of a Novel Model for Studying the Effects of Extracts of Chinese Herb Medicine on Human Type II 5α-Reductase in Vitro", YAKUGAKU ZASSHI 130(9) 1207-1214, (2010)

(non-patent literature 0002) Gupta S R et al., "Anti-arthritic activity of various extracts of *Sida rhombifolia* aerial parts", Natural Product Research: Formerly Natural Product Letters, 23:8, 689-695, (2009)

(non-patent literature 0003) Vaibhav M. Shinde et. al., "Hypoglycemic and Hypolipidemic Effect of *Sida rhombifolia* ssp. *retusa* in Diabetic Induced Animals", International Journal of Phytomedicine 2 (2010) 160-165

(non-patent literature 0004) Chaves O S et al., "Alkaloids and Phenolic Compounds from *Sida rhombifolia* L. (Malvaceae) and Vasorelaxant Activity of Two Indoquinoline Alkaloids", Molecules 2017; 22:1-9

DISCLOSURE

Technical Problem

Accordingly, the present disclosure has been made keeping in mind the above problems occurring in the prior art, and an objective of the present disclosure is to provide a novel use of *Sida rhombifolia*.

The problems to be solved by the present disclosure are not limited to the problems mentioned above, and other problems not mentioned will be clearly understood by those skilled in the art from the following description.

Technical Solution

The present inventors surprisingly found that *Sida rhombifolia* has an effect on benign prostatic hyperplasia and completed the present disclosure.

In order to accomplish the above object, the present disclosure provides a use of *Sida rhombifolia* as a medicament and/or food for treating, preventing, ameliorating, and/or inhibiting benign prostatic hyperplasia. Treatment is meant to encompass amelioration or mitigation of symptoms associated with benign prostatic hyperplasia, and prevention is meant to encompass inhibition of progression from a pre-state of a disease to a corresponding disease.

In one embodiment, the present disclosure provides a pharmaceutical composition comprising *Sida rhombifolia* as an active ingredient for treating or preventing benign prostatic hyperplasia.

The *Sida rhombifolia* (a.k.a *Sida rhombifolia* L.) is an annual herb, and its place of origin is tropical Asia.

The *Sida rhombifolia* may be a whole plant or a part of *Sida rhombifolia*, for example, it may be one or more selected from leaves, flowers, fruits, stems or roots.

The *Sida rhombifolia* may be one or more selected from raw *Sida rhombifolia*, a dried product of *Sida rhombifolia*, or a solvent extract of *Sida rhombifolia*.

The solvent may be a polar solvent.

The solvent may be one or more selected from water, alcohol, or a mixture thereof.

The alcohol may be a lower alcohol and may be one or more selected from alcohols having 1 to 5 carbon atoms. More preferably, the alcohol may be one or more selected from methanol and ethanol.

The benign prostatic hyperplasia may be caused by one or more selected from the activity of 5-alpha reductase (5AR), the expression of 5-alpha reductase, and the production of dihydrotestosterone (DHT).

The activity of the 5-alpha reductase may be an overactivity of the 5-alpha reductase.

The expression of the 5-alpha reductase may be overexpression of the 5-alpha reductase.

The production of the dihydrotestosterone may be an overproduction of the dihydrotestosterone.

The treatment or prevention may be achieved by one or more selected from inhibition of prostate cell division, inhibition of prostate tissue hypertrophy, inhibition of 5-alpha reductase activity, inhibition of 5-alpha reductase expression, and inhibition of dihydrotestosterone production by the *Sida rhombifolia*.

The inhibition of 5-alpha reductase expression may be inhibition of type 2 5-alpha reductase (5AR2 or 5AR Type II) expression.

In addition, the present disclosure provides a food composition comprising the *Sida rhombifolia* as an active ingredient for amelioration or inhibition of benign prostatic hyperplasia.

Unless otherwise stated, the food composition is equally applied as long as the matters mentioned in the pharmaceutical composition of the present disclosure are not contradictory. The "amelioration" is included in "treatment" and means that conditions or symptoms are reduced. The above "inhibition" is included in "prevention" and means suppressing the occurrence of conditions or symptoms.

The present disclosure also provides a method for treating, preventing, ameliorating, or inhibiting benign prostatic hyperplasia by administering *Sida rhombifolia* to an animal, including a human or non-human.

The animal may be a mammal.

The animal may be an animal in need of being administered *Sida rhombifolia*.

The animal may be an animal that has or is at the risk of having prostatic hyperplasia.

In addition, the *Sida rhombifolia* to be administered may be an effective amount of *Sida rhombifolia*.

In addition, the present disclosure provides use of *Sida rhombifolia* for preparing a formulation for treating or preventing benign prostatic hyperplasia.

Unless otherwise stated, each of the matters mentioned in the pharmaceutical composition, the food composition, the method, and the use of the present disclosure are equally applied unless they contradict each other.

The *Sida rhombifolia* or the composition can be administered orally or parenterally to a mammal including humans, and the active ingredient can be combined with a pharmaceutically acceptable carrier, and then can be formulated and administered. For formulation, commonly used fillers, extenders, binders, wetting agents, disintegrants, surfactants, diluents or excipients may be used. Solid formulations for oral administration include tablets, pills, powders, granules, capsules, etc., and such solid formulations can be prepared by adding at least one excipient, for example starch, calcium carbonate, sucrose, lactose, and/or gelatin, to the composition of the present disclosure. In addition, a lubricant such as magnesium or talc may be used. Liquid formulations for oral administration include suspensions, internal solutions, emulsions, and syrups, etc., and in addition to commonly used simple diluents such as water and liquid paraffin, various additives such as wetting agents, sweeteners, fragrances, and/or preservatives may be included. Formulations for parenteral administration include injectable solutions, suspensions, emulsions, lyophilisates, nasal washes, and suppositories. Injectable solutions, suspensions, and emulsions can be prepared by mixing water, non-aqueous solvents, or suspending agents with active ingredients. Non-aqueous solvents and suspending agents may be propylene glycol, polyethylene glycol, vegetable oils such as olive oil, and an injectable ester such as ethyl oleate. As the base of the suppository, witepsol, macrogol, Tween 61, cacao butter, laurin fat, glycerol, and/or gelatin may be used. When administered parenterally, the formulations can be administered by subcutaneous injection, intravenous injection, or intramuscular injection.

The food composition may be variously included in food including beverages, and may be in the form of beverages, gum, tea, health functional food, etc., and the health functional food may be formulated in dosage forms such as tablets, capsules, and the like. The term "health functional food" includes food manufactured (hereinafter, including "processed") using raw materials or ingredients useful for the human body in accordance with the Health Functional Food Act of the Republic of Korea, and the term "functional" refers to regulating nutrients or obtaining effects useful for healthcare, such as obtaining better physiological actions in relation to the structure and the function of the human body. The food composition may include conventional food additives, and the food additives may be mentioned of chemical compounds such as ketones, glycine, sodium citrate, nicotinic acid, and cinnamic acid, natural additives such as persimmon pigment, licorice extract, crystalline cellulose, sorghum color, and guar gum, and mixed additives such as sodium L-glutamate, alkalis added to noodles, preservatives, and tar colorants. In addition, the food composition is meant to include food additives and the like.

Each of the matters mentioned in the pharmaceutical composition and the food composition of the present disclosure are applied equally unless they contradict each other.

The *Sida rhombifolia* can be formulated by adding additives such as pharmaceutically or food scientifically acceptable carriers, excipients or diluents, and for information on formulation, references widely known in the art can be referred to.

Accordingly, the composition of the present disclosure may further include a pharmaceutically acceptable additives or a food-scientifically acceptable additives, and may consist of the active ingredient, the pharmaceutically acceptable additives, or the food-scientifically acceptable additives.

The composition of the present disclosure may contain 0.01 to 99.99% by weight of the active ingredient.

The *Sida rhombifolia* comprised in the present composition or used in the use or the method of the present disclosure can be used in a dose of 100 to 2000 mg per day on an adult body weight basis (60 kg), wherein the *Sida rhombifolia* may preferably be the solvent extract of *Sida rhombifolia*. Administration may be carried out once or divided into several times a day. However, the scope of the present disclosure is not limited by the dose and frequency of administration.

Advantageous Effects

According to the present disclosure, the treatment, prevention, amelioration, or inhibition of benign prostatic hyperplasia can be achieved.

MODE FOR INVENTION

Figure 1:
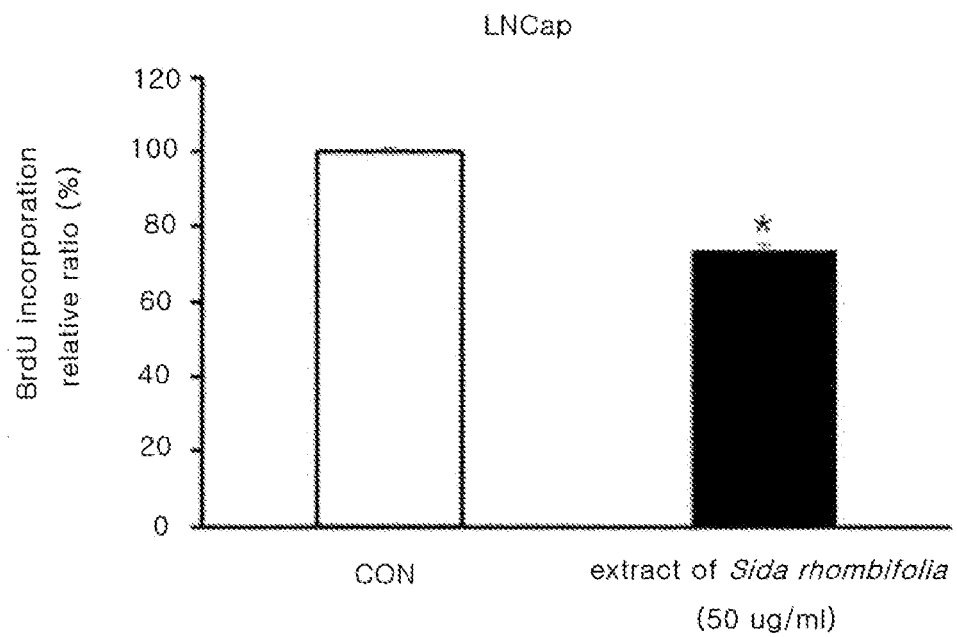
FIG. 1 is a graph showing the result of analyzing the effect of *Sida rhombifolia* on the inhibition of cell division in prostate cell lines.

Hereinafter, the advantages and features of the present disclosure and a method for achieving them, will become apparent with reference to the embodiments described below in detail in conjunction with the accompanying drawings. However, the present disclosure is not limited to the embodiments disclosed below but will be implemented in various different forms, and only these embodiments allow the disclosure of the present disclosure to be complete, and are provided only to fully inform a person of ordinary skill in the technical field to which the present disclosure belongs of the scope of the invention, and the present disclosure is only defined by the scope of the claims.

Throughout the specification "and/or" includes each of the recited elements, and all combinations of one or more of the recited elements.

The terminology used herein is for the purpose of describing the embodiments and is not intended to limit the present disclosure. In this specification, the singular also includes the plural, unless specifically stated otherwise in the phrase. As used herein, "comprises" and/or "comprising" does not exclude the presence of one or more other components and/or steps, or the addition of one or more other components and/or steps to the recited components and/or steps.

In the present specification, "raw Sida rhombifolia" means a whole plant or a part of Sida rhombifolia that has not undergone a separate drying process after collection, and "dried product of Sida rhombifolia" refers to a dried product of the raw Sida rhombifolia.

In addition, "solvent extract of Sida rhombifolia" means that one or more selected from raw Sida rhombifolia or a dried product of Sida rhombifolia extracted with a solvent, wherein "solvent extract of Sida rhombifolia" has the same meaning as "Sida rhombifolia extract".

Hereinafter, in Examples, it was revealed that Sida rhombifolia was effective in benign prostatic hyperplasia using prostate cell lines and experimental animals.

As reagents used in Examples, the commercially available best-graded reagents were used, and those purchased from Sigma Ltd. etc. were used.

EXAMPLE 1. CONFIRMATION OF USE OF Sida rhombifolia (I)

1-1. Preparation of Sida rhombifolia 1 liter of 100%-MeOH (HPLC grade) was added to a dried product of Sida rhombifolia (obtained from International Biological Material Research Center, Korea Research Institute of Bioscience and Biotechnology), which was prepared by drying leaves of Sida rhombifolia collected in Costa Rica, 2017, and grinding them. After that, ultrasound-assisted extraction was carried out at a temperature of 40° C. The extract obtained by repeating the extraction 3 times (for 2 hours per 1 extraction) was concentrated with a reduced pressure concentrator (Buchi R-220) to prepare a solvent extract of Sida rhombifolia.

1-2. Preparation of Cells

Prostate cell line LNCap cells were obtained from the Korean Cell Line Bank and used. Cells were maintained in Dulbecco's modified Eagle's medium (DMEM) supplemented with 10% heat-inactivated fetal bovine serum (FBS), penicillin (P/S), and streptomycin, under an incubating condition of 5%-$CO_2$ and 37° C.

1-3. Analysis of the Ability of Inhibition of Prostate Cell Division

In order to analyze the effect of Sida rhombifolia on the inhibition of prostate cell division, 5-bromo-2'-deoxyuridine (BrdU) incorporation assay was used. The BrdU incorporation assay is a test method that detects newly synthesized DNA in proliferating cells with a BrdU antibody, and can determine whether a test substance inhibits cell division. By using this BrdU incorporation assay, the effect of Sida rhombifolia on the inhibition of prostate cell division was analyzed.

100 ul of the cells ($2 \times 10^5$ cells/ml) prepared as in 1-2. were seeded in each well of 96-well plate, and 24 hours later the solvent extract of Sida rhombifolia prepared as in 1-1. was dissolved in dimethyl sulfoxide (DMSO) to a concentration of 100 mg/ml, and was diluted with a cell culture to a final concentration of 50 ug/ml. The degree of BrdU incorporation was measured using a kit (Abeam, ab126556). After 2 hours of processing the extract, 20 ul of BrdU label reagent was added thereto and incubated the mixture for 24 hours. After the cell culture was completely removed, 200 ul of a fixing solution was added thereto and the mixture was left at ambient temperature for 30 minutes. After that, the fixing solution was removed and the mixture was dried. After washing the dried mixture twice with phosphate buffer saline (PBS), 100 ul of anti-BrdU monoclonal detector antibody was added thereto and the mixture was left at ambient temperature for 1 hour. After the solution was removed and a residue was washed, Peroxidase Goat Anti-Mouse IgG was added thereto and the mixture was left for 30 minutes, and then washed. 100 ul of 3,3', 5,5'-Tetramethylbenzidine (TMB) peroxidase substrate was added thereto and the mixture was allowed to react at ambient temperature for 30 minutes in a light-shielded state, and then 100 ul of stop solution was added thereto, thereby terminating the reaction. The degree of BrdU incorporation was measured with a multi-well spectrometer (Tecan, Infinite) at a test wavelength of 450/540 nm. The control group was treated in the same manner as the group treated with the solvent extract of Sida rhombifolia, except that PBS was used instead of the solvent extract of Sida rhombifolia. From the quantitative results, the BrdU incorporation ratio (%) compared to that of the control group was calculated, and the results are shown in FIG. 1.

FIG. 1 is a graph showing the results of analysis of the effect of Sida rhombifolia on the inhibition of cell division of prostate cell lines. The x-axis represents the control group (CON) and the group treated with the solvent extract of Sida rhombifolia (Sida rhombifolia extract), and the y-axis represents the BrdU incorporation as a percentage (relative ratio %) compared to that of the control group (*$p<0.1$; compared with the control group).

As shown in FIG. 1, it can be found that *Sida rhombifolia* significantly inhibited cell division of the prostate cell line. From these results, it can be found that *Sida rhombifolia* is effective in suppressing benign prostate hyperplasia by inhibition of prostate cell division. This is because *Sida rhombifolia* can inhibit benign prostatic hyperplasia, which is prostatic hypertrophy due to cell division.

As a result, it can be found that the present disclosure can provide a use of *Sida rhombifolia* as a medicament and/or food for treating, preventing, ameliorating, and/or inhibiting benign prostatic hyperplasia.

EXAMPLE 2. CONFIRMATION OF USE OF *Sida rhombifolia* (II)

5-alpha reductase (5AR) is the most important enzyme that mediates the conversion of testosterone into dihydrotestosterone (DHT). DHT is known to play the most important role in the growth of prostate tissue. Therefore, this study was intended to determine whether *Sida rhombifolia* has an effect on benign prostatic hyperplasia by confirming whether *Sida rhombifolia* inhibits 5AR activity or not.

2-1. Preparation of *Sida rhombifolia*

In the same manner as in Example 1-1., a solvent extract of *Sida rhombifolia* was prepared.

2-2. Preparation of Enzyme Source

In order to prepare the 5AR enzyme source, first, 15-week-old Sprague Dawley rats (obtained from Coretech) were kept under $CO_2$ inhalation anesthesia, and then the prostate tissue was excised. After washing 200 mg of the excised tissue twice with PBS at pH 7.4, 10 ml of lysis buffer {20 mM sodium phosphate containing 0.32 M sucrose and 1 mM ethylenediaminetetraacetic acid (EDTA) at pH 6.5} was added, followed by homogenizing the mixture by a glass homogenizer. The homogenate was centrifuged at 4° C. and 5,000 rpm for 15 minutes to take the supernatant and quantify a protein using Brad Ford reagent, and then the protein was used as a 5AR enzyme source. The remaining homogenate was stored at −70° C.

2-3. Analysis of the Ability of Inhibition of 5AR Activity

The ability to inhibit 5AR activity was measured using the method of Nahata and Dixit {Andrologia, 46(6):592-601, 2014}. In a 96-well plate, the enzyme source (0.8 mg/ml protein) prepared as in 2-2, a solution obtained by dissolving the solvent extract prepared in 2-1. in methanol (50 ug/ml), 7.5 mM testosterone, and 300 uM β-NADPH were reacted at 37° C. Thereafter, absorbance according to the change in the amount of β-NADPH at 350 nm was measured every 5 minutes for a total of 30 minutes. The measurement value was calculated using a standard graph of β-NADPH, and the unit was expressed as pg/ml. The blank sample was prepared in the same manner as in the group treated with the solvent extract of *Sida rhombifolia*, except that methanol was used instead of the solvent extract of *Sida rhombifolia* and phosphate buffer was used instead of testosterone. A negative control group was prepared in the same manner as the group treated with the solvent extract of *Sida rhombifolia* except that methanol was used instead of the solvent extract of *Sida rhombifolia*. A positive control group was prepared in the same manner as the group treated with the solvent extract of *Sida rhombifolia*, except that finasteride (100 uM) was used instead of the solvent extract of *Sida rhombifolia*. Since 5AR in the enzyme source converts β-NADPH to β-NADP, the amount of β-NADPH in the reaction solution tends to decrease during the reaction time. On the other hand, when a substance that inhibits 5AR activity is treated, the amount of β-NADPH does not change or its concentration tends to increase gradually as NADPH freely escapes from the binding site of the enzyme. Therefore, it can be found that the higher the concentration of β-NADPH at the end of the reaction, the better the ability of the sample to inhibit 5AR activity.

Figure 2:
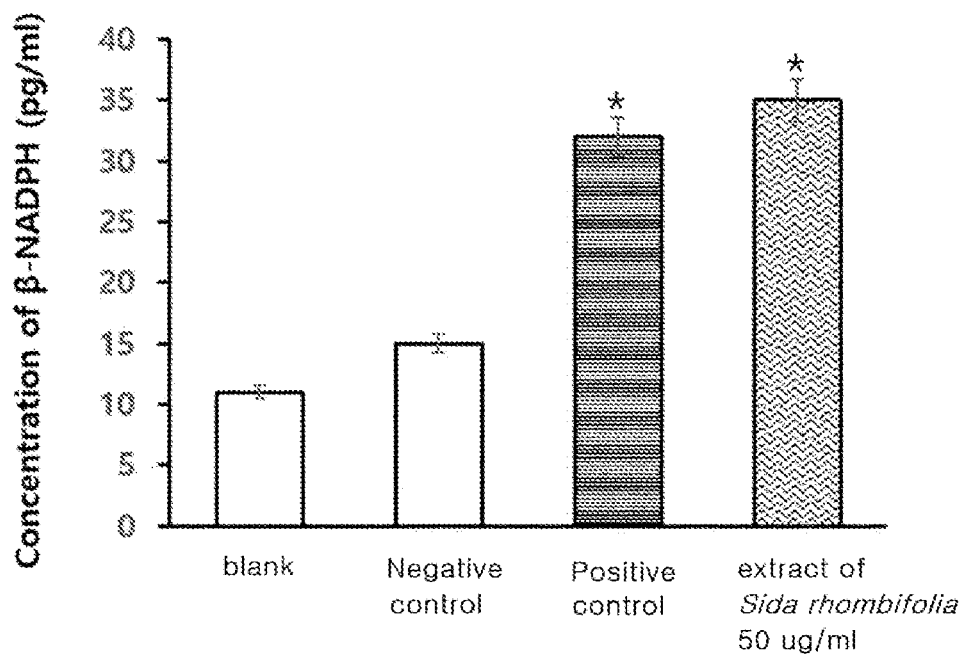
FIG. 2 is a graph showing the results of analysis of the effect of *Sida rhombifolia* on the inhibition of 5AR activity.

FIG. 2 is a graph showing the results of analysis of the effect of *Sida rhombifolia* on the inhibition of 5AR activity. The x-axis represents a blank sample, a negative control group, a positive control group, and a group treated with the solvent extract of *Sida rhombifolia* (*Sida rhombifolia* extract), and the y-axis represents the concentration of β-NADPH in the reaction solution at the end of the reaction. (*$p<0.01$; compared with the negative control).

As shown in FIG. 2, in the case of the positive control group treated with finasteride, it was confirmed that the concentration of β-NADPH increased compared to that in the negative control group, indicating that the 5AR enzyme activity was inhibited. It can be found that in the case of the group treated with the solvent extract of *Sida rhombifolia*, the concentration of β-NADPH increased compared to that in the positive control group, indicating that the 5AR enzyme activity was significantly inhibited.

From these results, it can be found that *Sida rhombifolia* significantly inhibits the activity of 5AR. Therefore, it can be found that *Sida rhombifolia* is effective for suppressing benign prostatic hyperplasia by inhibition of 5AR activity.

As a result, it can be found that the present disclosure can provide a use as a medicament and/or food for treating, preventing, ameliorating and/or inhibiting benign prostatic hyperplasia.

EXAMPLE 3. CONFIRMATION OF USE OF *Sida rhombifolia* (III)

3-1. Preparation of *Sida rhombifolia*

A dried product of *Sida rhombifolia* (obtained from International Biological Material Research Center of Korea Research Institute of Bioscience and Biotechnology), which was prepared by drying leaves of *Sida rhombifolia* collected in Costa Rica, 2017, and grinding them was extracted using three types of solvents. In particular, 100 ml of 50%-EtOH (HPLC grade) or 100%-EtOH (HPLC grade) was added to 1 g of a dried product of *Sida rhombifolia*, and the extraction was carried out at a temperature of 80° C. In addition, 100 ml of hot water was added to 1 g of the dried product of *Sida rhombifolia*, and the extraction under reflux was carried out at 100° C. Thereafter, each extract extracted for 3 hours was concentrated with a reduced pressure concentrator (Buchi R-220), to prepare a solvent extract of *Sida rhombifolia*

3-2. Preparation of Experimental Animals

As the experimental animals, 6-week-old male Wistar rats were used. The breeding environment of the experimental animals was a temperature of 23±3° C., a relative humidity of 55±5%, and a light-dark shift of about 12 hours, and feed and water were freely provided. Experimental animals were housed two per breeding box, and then weighing and changing of bedding were carried out once every 5 days for management.

After one week of acclimatization, the animals were castrated to exclude the effects of intrinsic testosterone. Experimental animals were anesthetized with isoflurane and secured having their back side facing the operator, and the skin at the end of the scrotum was incised to cut off the left and right testicles and epididymis. After that, the incision was sutured to complete surgery. All experimental animals were administered antibiotics (cefazolin) and analgesics (carprofen) before surgery to relieve inflammation and pain. After castration, the animals were stabilized for 7 days to heal the wound at the surgical site, and the experiment was started as described below. The weight of the animals at the time of initiation was set to an average of 200-250 g in each group, and the number of experimental animals per group was 8. During the experiment, different groups were placed so that they were not in the same cage, and water and feed were freely provided.

3-3. Treatment of Laboratory Animals

To the experimental animals prepared as in 3-2., testosterone propionate (TP) was injected subcutaneously at a dose of 3 mg/kg body weight once a day for a total of 6 weeks to induce prostatic hypertrophy, thereby preparing a benign prostatic hyperplasia induction group. In this case, TP was used by being dissolved in peanut oil, so that the total injection volume was 100 µl based on the weight of the experimental animal measured every 3 days in order to minimize the error of the experiment. In order to evaluate the amelioration effect of benign prostatic hyperplasia achieved by *Sida rhombifolia* extract, TP was injected subcutaneously and each of 3 types of *Sida rhombifolia* extracts prepared in 3-1. was diluted in 0.5%-carboxy methylcellulose (CMC), and was orally administered at a dose of 100 mg/kg body weight/day. In addition, the positive control group was treated in the same manner as the group treated with the solvent extract of *Sida rhombifolia*, except that Saw palmetto diluted in peanut oil was orally administered at 100 mg/kg body weight/day instead of the diluted solvent extract of *Sida rhombifolia*. The control group was treated in the same manner as the group treated with the solvent extract of *Sida rhombifolia*, except that 0.5%-CMC was orally administered at 10 ml/kg body weight/day instead of the diluted solvent extract of *Sida rhombifolia*.

3-4. Final Weighing, Necropsy, and Sampling of Experimental Animals

After 6 weeks of experimentation, the experimental animals were fasted for 16 hours and the final body weight was measured. Thereafter, the experimental animals were euthanized by cervical dislocation, and then the prostate (dorsal prostate and ventral prostate) and bladder were excised, carefully separated, washed once with PBS, and then water was slightly removed therefrom.

3-5. PI Analysis

In order to confirm whether *Sida rhombifolia* inhibits prostate tissue hypertrophy, PI (Prostate index) was analyzed.

The weight of the prostate excised in 3-4. was measured. From the measured prostate weight and the final body weight measured in 3-4, PI was calculated by the following formula. The results are shown in FIG. 3.

$$PI=\{\text{weight (g) of prostate excised/final body weight (g)}\} \times 100$$

Figure 3:
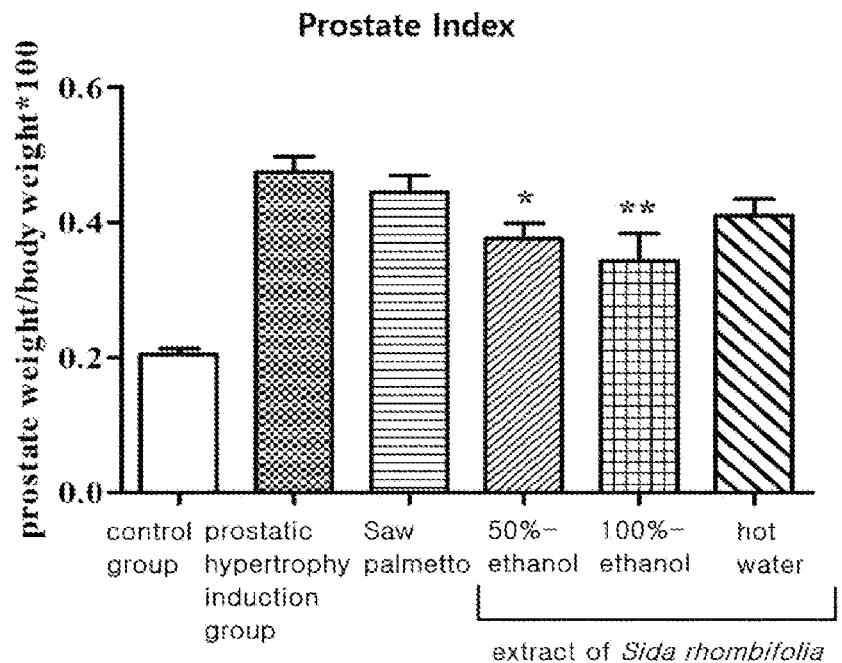
FIG. 3 is a graph showing the results of analysis of the effect of Sida rhombifolia on the inhibition of prostate tissue hypertrophy.

FIG. 3 is a graph showing the results of analysis of the effect of *Sida rhombifolia* on the inhibition of prostate tissue hypertrophy. In the graph of FIG. 3, the y-axis represents PI (Prostate weight/body weight*100) (*p<0.1; compared with the control group, **p<0.01: compared with the control group).

As shown in FIG. 3, in the case of a positive control group, the PI tended to decrease by saw palmetto. In the case of the group treated with the solvent extract of *Sida rhombifolia*, in particular the group treated with 50%-ethanol extract and the group treated with 100%-ethanol extract, it can be found that the PI significantly decreased compared to that of the positive control group. From these results, it can be found that *Sida rhombifolia* inhibits the prostate tissue hypertrophy.

3-6. Analysis of 5AR and DHT in Prostate Tissue

In order to confirm whether *Sida rhombifolia* inhibits the expression of 5AR (in particular, 5AR2 mainly expressed in the prostate) and inhibits the production of DHT, Enzyme-Linked ImmunoSorbent Assay (ELISA) was used. In particular, ELISA was performed using the 5AR2 ELISA kit (Cusabio, #CSB-EL022654RA) and the DHT ELISA kit (Mybiosource, #MBS266535) according to the manufacturer's instructions.

The prostate tissue excised in 3-4. was homogenized to obtain a homogenate, and the expression level of 5AR2 and the production amount of DHT were analyzed using an ELISA kit.

For the measurement of 5AR expression level, 50 µul of the homogenate was mixed well with HRP-conjugated SRD5A2 (rat 3-oxo-5-alpha-steroid-4-dehydrogenase 2) and SRD5A2-specific antibody in a 96-well microplate pre-coated with goat-anti-rabbit antibody, and shaking incubation was carried out at 37° C. for 1 hour. After incubation, the substrate solution was added thereto, and the reaction was stopped with sulfuric acid solution after 15 minutes. Then the difference was measured for each sample within 10 minutes at 450 nm. Calculation of the measured value uses a standard graph, and the unit is expressed as pg/mL. The results are shown in FIG. 4.

To measure the production amount of DHT, 50 µl of the homogenate was shaking incubated with HRP-conjugated DHT and DHT-specific antibody in a 96-well microplate pre-coated with goat-anti-rabbit antibody for 1 hour at room temperature. After incubation, the substrate solution was added thereto, and the reaction was stopped with sulfuric acid solution after 15 minutes. Then the difference was measured for each sample within 10 minutes at 450 nm. Calculation of the measured value uses a standard graph, and the unit is expressed as pg/mL. The results are shown in FIG. 5.

Figure 4:
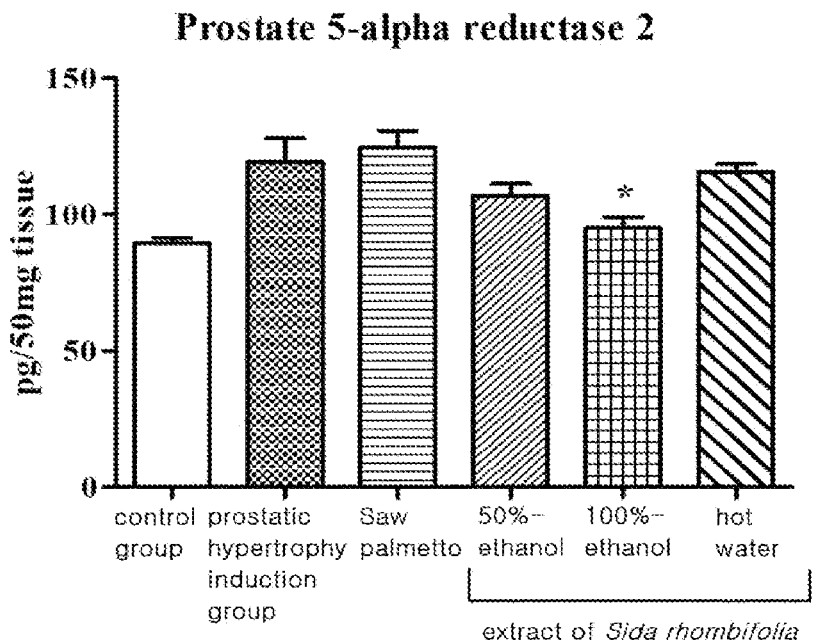
FIG. 4 is a graph showing the results of analysis of the effect of Sida rhombifolia on the inhibition of 5AR expression.
Figure 5:
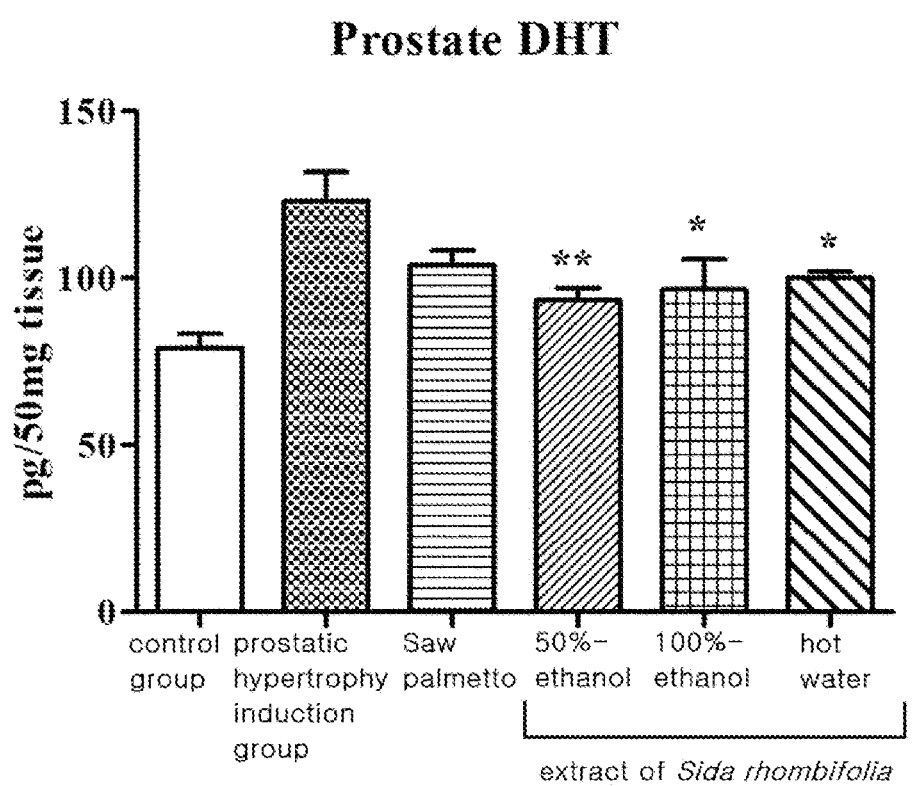
FIG. 5 is a graph showing the results of analysis of the effect of Sida rhombifolia on the inhibition of DHT production.

FIG. 4 is a graph showing the results of analysis of the effect of *Sida rhombifolia* on the inhibition of 5AR expression, and FIG. 5 is a graph showing the results of analyzing the effect of the *Sida rhombifolia* on the inhibition of DHT production. The y-axis of FIG. 4 represents the expression level of 5AR2, and the y-axis of FIG. 5 represents the production amount of DHT (*p<0.1; compared with the control group, **p<0.01: compared with the control group).

As shown in FIGS. 4 to 5, in the case of the group treated with the solvent extract of *Sida rhombifolia*, the expression level of 5AR2 and the production amount of DHT were significantly reduced compared to that of the prostate hypertrophy induction group, and it can be found that this treatment is effective even compared to the treatment in the positive control group.

From these results, it can be found that *Sida rhombifolia* inhibits 5AR2 expression and inhibits DHT production. Therefore, it can be found that *Sida rhombifolia* is effective in ameliorating benign prostatic hyperplasia by inhibition of 5AR expression and DHT production.

As a result, it can be found that the present disclosure can provide a use of *Sida rhombifolia* as a medicament and/or a food for treating, preventing, ameliorating, and/or inhibiting benign prostatic hyperplasia.

In particular, such treatment, prevention, amelioration, and/or inhibition may be, as specifically shown in the experimental results, achieved by one or more selected from inhibition of prostate cell division, inhibition of prostate tissue hypertrophy, inhibition of 5-alpha reductase activity, inhibition of 5-alpha reductase expression, and inhibition of dihydrotestosterone production by *Sida rhombifolia*.

PREPARATION EXAMPLE 1. PRODUCTION OF PHARMACEUTICAL COMPOSITION

Capsules were prepared by filling a gelatin capsule with 100 mg of a solvent extract of *Sida rhombifolia* prepared in the same manner as in Example 3-1, 100 mg of corn starch, 100 mg of lactose, and 2 mg of magnesium stearate.

PREPARATION EXAMPLE 2. PRODUCTION OF FOOD COMPOSITION

Water was added to the solvent extract of *Sida rhombifolia* prepared in the same manner as in Example 3-1. (10% by weight), liquid fructose (0.5% by weight), oligosaccharide (2% by weight), sugar (2% by weight), and salt (0.5% by weight) in order to balance the mixture, followed by mixing them homogeneously, and instantaneously sterilize the mixture to prepare a health drink.

INDUSTRIAL APPLICABILITY

As described above, the present disclosure may be achieved by an effective treatment, prevention, amelioration and/or inhibition of prostatic hyperplasia, and may be said to have an industrial applicability.

The invention claimed is:

1. A method of treating, ameliorating, or inhibiting benign prostatic hyperplasia, the method comprising administering an effective amount of *Sida rhombifolia* to a subject in need thereof, wherein the *Sida rhombifolia* is prepared as a solvent extract and the treating, the ameliorating, or the inhibiting is achieved by at least one effect selected from inhibition of 5-alpha reductase activity, inhibition of 5-alpha reductase expression, and inhibition of dihydrotestosterone production.

2. The method according to claim 1, wherein the subject is a non-human animal.

3. The method according to claim 1, wherein the subject is a human.

4. The method according to claim 1, the solvent comprises at least one selected from water, ethanol, or a mixture thereof.

* * * * *